United States Patent
Suzuki et al.

(10) Patent No.: US 10,238,356 B2
(45) Date of Patent: Mar. 26, 2019

(54) X-RAY COMPUTED TOMOGRAPHY APPARATUS AND MEDICAL IMAGE DISPLAY APPARATUS

(71) Applicant: Toshiba Medical Systems Corporation, Otawara-shi (JP)

(72) Inventors: Yojiro Suzuki, Otawara (JP); Katsuhiko Ishida, Nasushiobara (JP); Takahiro Yoda, Nasushiobara (JP); Katsuhito Morino, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/715,953

(22) Filed: May 19, 2015

(65) Prior Publication Data
US 2015/0327825 A1 Nov. 19, 2015

(30) Foreign Application Priority Data
May 19, 2014 (JP) .................. 2014-103811

(51) Int. Cl.
*A61B 6/00* (2006.01)
*A61B 6/03* (2006.01)
(Continued)

(52) U.S. Cl.
CPC ............ *A61B 6/5258* (2013.01); *A61B 6/032* (2013.01); *A61B 6/035* (2013.01); *A61B 6/463* (2013.01);
(Continued)

(58) Field of Classification Search
None
See application file for complete search history.

(56) References Cited

U.S. PATENT DOCUMENTS 5,459,769 A * 10/1995 Brown .................. A61B 6/032
378/16
5,668,846 A * 9/1997 Fox ........................ A61B 6/464
378/4
(Continued)

FOREIGN PATENT DOCUMENTS

JP 6-114049 4/1994
JP 2006-320464 11/2006
(Continued)

OTHER PUBLICATIONS

RSNA, "X-ray: Exhibit reference to "Spot Fluoroscopy" technology", Toshiba Medical Systems, downloaded from www.innervision.co.jp/rsna2011/toshiba/xray.html, 2011.*

*Primary Examiner* — Michael J Logie
(74) *Attorney, Agent, or Firm* — Oblon, McClelland, Maier & Neustadt, L.L.P.

(57) ABSTRACT

According to an embodiment, X-ray CT apparatus includes X-ray generator includes X-ray tube, high-voltage generator, detector, controller and circuitry. High-voltage generator generates tube voltage to be applied to X-ray tube. Detector detects X-rays irradiated from X-ray tube and transmitted through a subject. Controller controls high-voltage generator to scan the subject with first radiation dose and with second radiation dose lower than first radiation dose. Circuitry generates first image based on projection data acquired by scan at first radiation dose, generates second image based on projection data acquired by scan at second radiation dose, and displays first image and second image in common window.

17 Claims, 17 Drawing Sheets

(51) Int. Cl.
  *H05G 1/08* (2006.01)
  *A61B 6/12* (2006.01)
(52) U.S. Cl.
  CPC ............. *A61B 6/481* (2013.01); *A61B 6/482* (2013.01); *A61B 6/488* (2013.01); *A61B 6/504* (2013.01); *A61B 6/5205* (2013.01); *A61B 6/542* (2013.01); *H05G 1/085* (2013.01); *A61B 6/12* (2013.01)

(56) References Cited

U.S. PATENT DOCUMENTS

| | | | | |
|---|---|---|---|---|
| 5,687,208 | A * | 11/1997 | Bae ..................... | G06F 19/3437 378/8 |
| 6,393,090 | B1 * | 5/2002 | Hsieh .................... | A61B 6/022 378/20 |
| 7,324,622 | B2 * | 1/2008 | Morikawa .............. | A61B 6/032 378/15 |
| 8,472,684 | B1 * | 6/2013 | Periaswamy ........ | G06K 9/6289 382/128 |
| 9,414,788 | B2 * | 8/2016 | Sung ..................... | A61B 6/022 |
| 2008/0144764 | A1 * | 6/2008 | Nishide ................ | A61B 6/4035 378/5 |
| 2011/0075905 | A1 * | 3/2011 | Noshi .................... | A61B 6/032 382/131 |
| 2012/0230462 | A1 * | 9/2012 | Robar .................. | A61N 5/1049 378/4 |
| 2013/0090554 | A1 * | 4/2013 | Zvuloni ............. | A61B 10/0241 600/424 |
| 2013/0223719 | A1 * | 8/2013 | Ohishi ................. | A61B 6/5235 382/132 |
| 2015/0078516 | A1 * | 3/2015 | Ohashi .................... | A61B 6/06 378/42 |
| 2015/0243056 | A1 * | 8/2015 | Lee ....................... | G06T 7/0028 382/131 |
| 2016/0310090 | A1 * | 10/2016 | Klinder ................ | A61B 6/5288 |

FOREIGN PATENT DOCUMENTS

| | | | |
|---|---|---|---|
| JP | 2011-19712 | 2/2011 | |
| JP | WO 2012046844 A1 * | 4/2012 | ........... A61B 6/5235 |
| WO | WO 2011/152070 A1 | 12/2011 | |
| WO | WO 2013/125276 A1 | 8/2013 | |

* cited by examiner

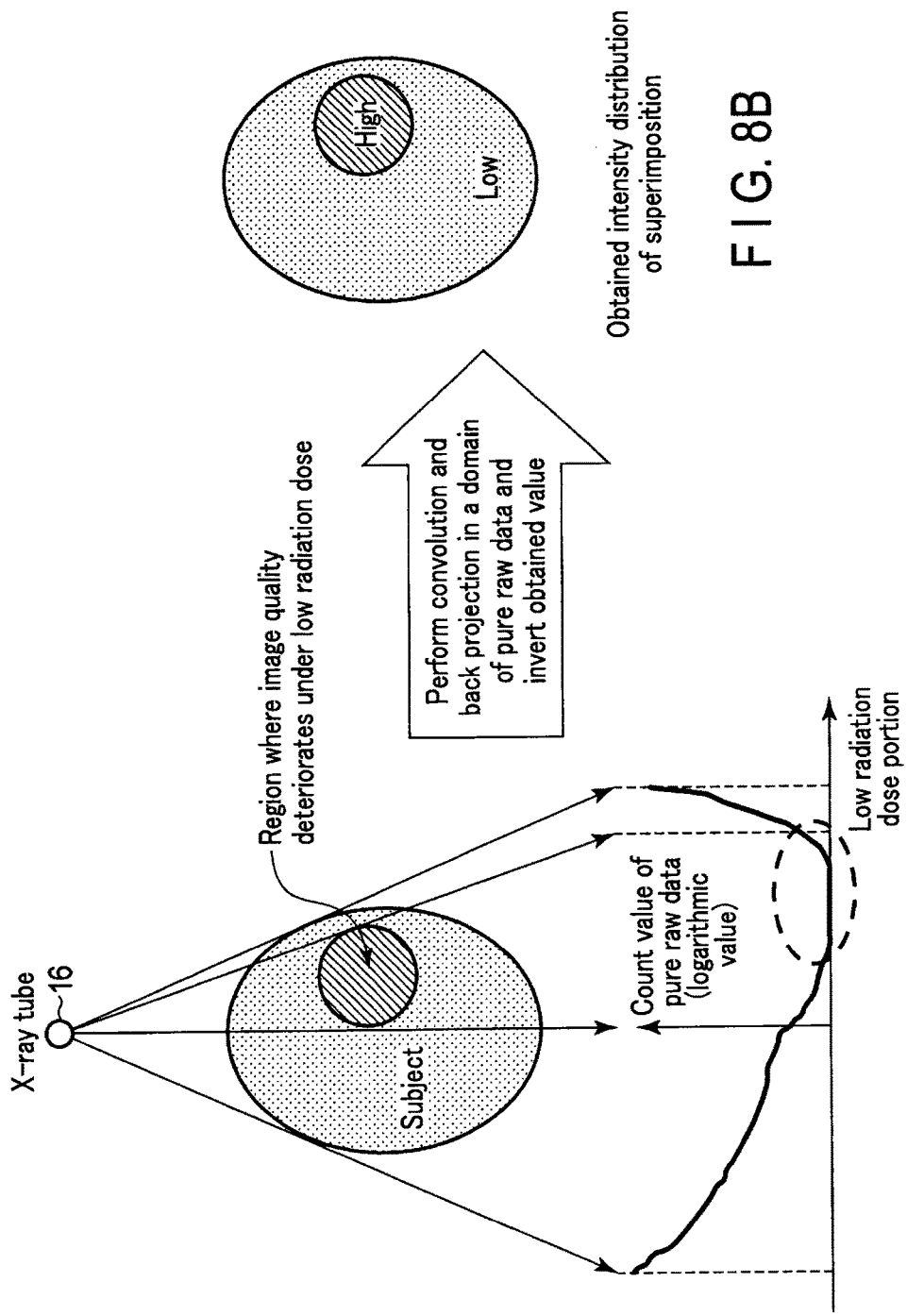
F I G. 8B
F I G. 8A

X-RAY COMPUTED TOMOGRAPHY APPARATUS AND MEDICAL IMAGE DISPLAY APPARATUS

CROSS-REFERENCE TO RELATED APPLICATIONS

This application is based upon and claims the benefit of priority from the Japanese Patent Application No. 2014-103811, filed May 19, 2014, the entire contents of which are incorporated herein by reference.

FIELD

The embodiments of the present invention relate to an X-ray computed tomography apparatus and a medical image display apparatus which is adaptable in the X-ray computed tomography apparatus.

BACKGROUND

An X-ray computed tomography apparatus (hereinafter described as an X-ray CT apparatus) processes by a computer data acquired by an X-ray scan of a subject and creates an image of the inside of the subject. In other words, the X-ray CT apparatus exposes the subject from various directions over a number of times, detects the X-rays transmitted through the subject by a detector, and acquires a plurality of detected data. The acquired detected data is subject to A/D (analog/digital) conversion by a data acquisition system, and is transmitted to a data processing system.

The data processing system forms projection data by applying preprocessing etc. to the detected data. The data processing system executes a reconstruction processing based on the projection data and forms tomographic image data. As a further reconstruction processing, the data processing system forms volume data based on a plurality of tomographic image data. The volume data is a data set expressing a three-dimensional distribution of a CT value corresponding to a three-dimensional region of the subject.

Several scanning schemes using an X-ray CT apparatus are known. For example, in imaging using a radiocontrast agent, a pre-scan, a main scan, and a monitoring scan are known. The pre-scan is executed before the radiocontrast agent is injected. The main scan is executed after the radiocontrast agent is injected, and when the radiocontrast agent is sufficiently permeated. Usually, an image obtained by the main scan is used for diagnosis.

The monitoring scan is a method for monitoring an image created on a real-time basis while scan imaging the subject so as to acquire a correct injection timing of the radiocontrast agent.

The monitoring scan is executed to monitor the density of the injected radiocontrast agent. The monitoring scan is executed after the radiocontrast agent is injected into the subject, and over a number of times before the radiocontrast agent is sufficiently permeated. The monitoring scan is executed between the pre-scan and the main scan.

When executing a CT fluoroscopy or a monitoring scan, a diagnostic reading doctor monitors the reconstructed CT image over a comparatively long time on a real-time basis. However, since the CT image used for monitoring is almost never used for diagnosis, the CT fluoroscopy and the monitoring scan are executed with the lowest X-ray radiation dose. In this manner, the radiation dose to which the subject is exposed can be minimized. Nevertheless, it is undeniable that various negative effects are caused by the low-dose irradiation.

For example, the CT image reconstructed from the scan data acquired under a low radiation dose includes significant image noise, which makes diagnostic reading difficult. Sometimes, by applying various image corrections, the CT value of a part of the image may drop significantly, causing the image quality to increasingly deteriorate. If an image including a deteriorated portion is used, the certainty and safety of the CT fluoroscopy and the monitoring scan may be hindered.

Furthermore, the lower the radiation dose when executing the CT fluoroscopy or the monitoring scan gets, the greater dependency would be placed on the skill of an individual operator or a diagnostic reading doctor. In the above manner, since low radiation dose imaging may deteriorate the visibility of an image or hinder reproducibility of a study, technical measures of some kind are demanded.

BRIEF DESCRIPTION OF THE DRAWINGS

FIG. 8A is a schematic diagram for supplemental explanation on an intensity distribution;

FIG. 8B is a schematic diagram for supplemental explanation on the intensity distribution;

DETAILED DESCRIPTION

In general, according to one embodiment, an X-ray computed tomography apparatus includes an X-ray generator includes an X-ray tube, a high-voltage generator, an X-ray detector, a controller and circuitry. The high-voltage generator generates a tube voltage to be applied to the X-ray tube. The X-ray detector detects X-rays irradiated from the X-ray tube and transmitted through a subject. The controller controls the high-voltage generator to scan the subject with a first radiation dose and with a second radiation dose which is lower than the first radiation dose. The circuitry generates a first image based on projection data acquired by the scan at the first radiation dose, generates a second image based on projection data acquired by the scan at the second radiation dose, and displays the first image and the second image in a common window.

Hereinafter, the X-ray CT apparatus according to the embodiments of the present application will be explained with reference to the drawings.

As one type of the X-ray CT apparatus, there is a ROTATE/ROTATE type, in which an X-ray tube and an X-ray detector are integrated and rotate around a subject. As another type of the X-ray CT apparatus, there is a STATIONARY/ROTATE type. The apparatus of the STATIONARY/ROTATE type comprises a plurality of detection elements arranged fixedly in a ring shape and an X-ray tube rotating around the subject. There are other various types of X-ray CT apparatuses.

The techniques explained hereinafter can be applied to any type of apparatus. In the following explanation, the ROTATE/ROTATE type is assumed.

As an image reconstruction method used for the X-ray CT apparatus, there are a full-scan method and a half-scan method. In the full-scan method, in order to reconstruct CT image data for one slice, projection data for a cycle around the subject, that is, approximately two $\pi$[rad], is required. In the half-scan method, in order to reconstruct image data for one slice, projection data for $\pi+\alpha$[rad] ($\alpha$: fan angle) is required. The technique according to the present embodiment can be applied to both the full-scan method and the half-scan method. In the following, explanations are made assuming the full-scan method.

Furthermore, in the following explanation, unless mentioned in particular, a CT scan indicates a monitoring scan. In the following explanation, a chest portion of a subject P is assumed as a scan region. The scan region may be any portion of the subject P as long as it is a region in which a radiocontrast agent can flow.

Figure 1:
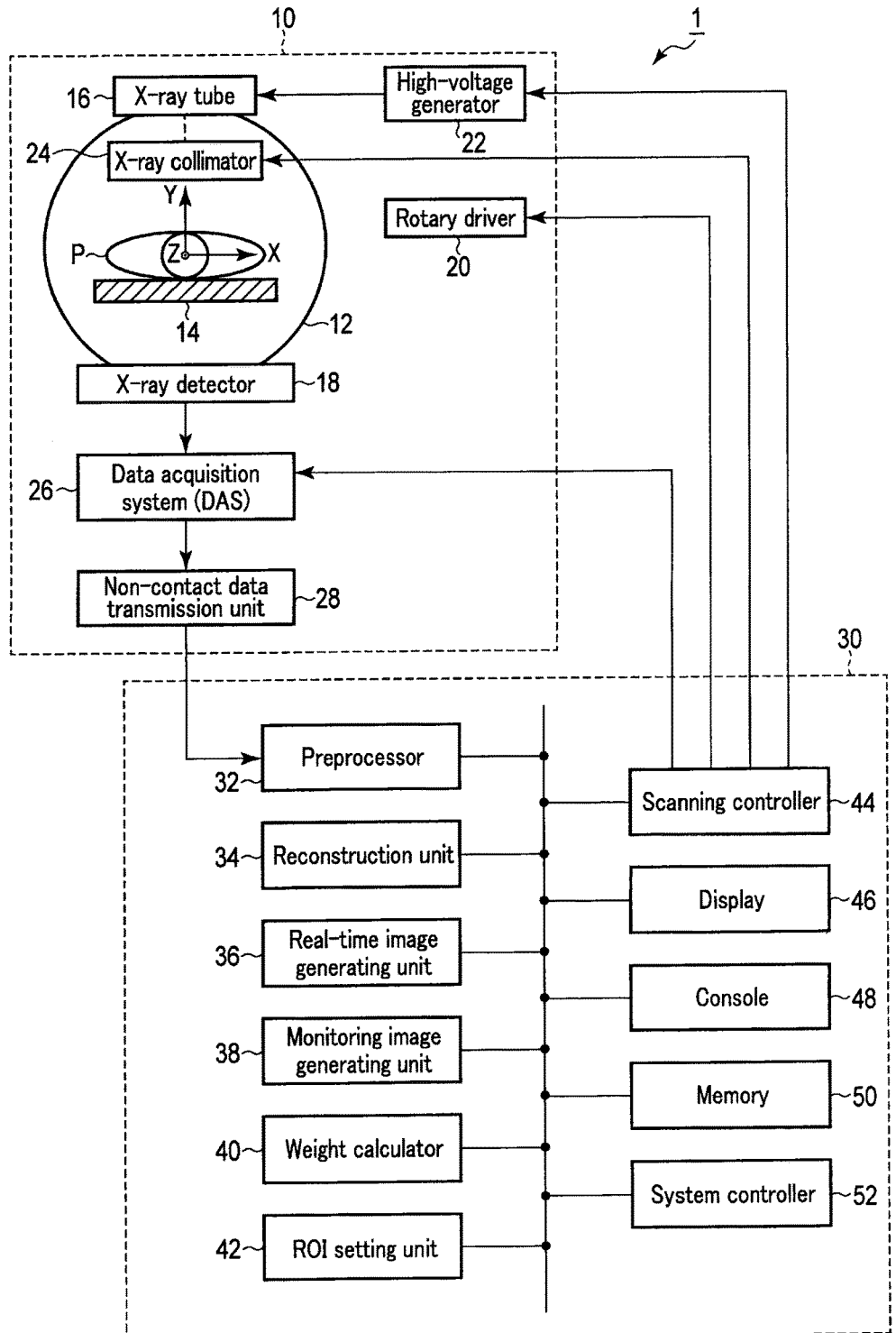
FIG. 1 is a diagram showing an example of an X-ray CT apparatus 1 according to an embodiment.

FIG. 1 is a diagram showing an example of an X-ray CT apparatus 1 according to an embodiment. The X-ray CT apparatus 1 comprises a scan unit (gantry) 10 and a computer 30.

The scan unit 10 has various mechanisms for performing a CT scan on the subject P by an X-ray. The scan unit 10 performs a CT scan repeatedly in accordance with the control by a scanning controller 44 in the computer 30.

The scan unit 10 rotatably supports a ring-shaped or a disk-shaped rotary frame 12. A scan region into which the subject P mounted on a top plate 14 is inserted is formed on an inner circumference side of the rotary frame 12. In this embodiment, a radiocontrast agent for visualizing a blood vessel on a CT image is injected into the subject P. The top plate 14 is slidably supported in a longitudinal direction and in a vertical direction by a bed (not shown).

Here, XYZ orthogonal coordinate systems are defined as follows. A Z-axis is defined as a rotating axis of the rotary frame 12. The longitudinal direction of the top plate 14 is arranged in parallel with the Z-axis direction. An X-axis is defined as an axis in a horizontal direction. A Y-axis is defined by an axis in a vertical direction.

The rotary frame 12 comprises an X-ray tube 16 and an X-ray detector 18 which face each other with the subject P mounted on the top plate 14 positioned in between. The rotary frame 12 rotates the X-ray tube 16 and the X-ray detector 18 continuously by a drive signal provided by a rotary driver 20.

The X-ray tube 16 generates an X-ray by a high voltage and a tube current provided from a high-voltage generator 22. The time interval of an X-ray irradiation to the subject is, for example, ten times per second. The high-voltage generator 22 applies a high voltage to the X-ray tube 16 and supplies a tube current in accordance with the control by the scanning controller 44 of the computer 30. Since the tube current changes by changing a voltage value, the radiation dose of the X-ray can be changed.

For example, the main scan for image diagnosis is performed at a tube current of 500 mA under the control by the scanning controller 44. The pre-scan performed for positioning a Region of Interest (ROI) etc. is performed at, for example, a tube current of 100 mA, which is lower than in the main scan under the control of the scanning controller 44. The monitoring scan for monitoring the density of the radiocontrast agent is performed at, for example, a tube current of 10 mA, which is significantly lower than in the pre-scan under the control of the scanning controller 44.

An X-ray collimator 24 is provided on an X-ray irradiation port side of the X-ray tube 16. The X-ray collimator 24 limits the radiation field of the X-ray generated by the X-ray tube 16. Specifically, the X-ray collimator 24 comprises a plurality of diaphragm blades which are movably supported. The material of the diaphragm blade is a substance which shields X-rays (such as lead). By adjusting the position of the plurality of diaphragm blades, the size and the shape of the X-ray radiation field may be changed. The X-ray collimator 24 moves the diaphragm blades based on the drive signal given from the scanning controller 44.

The X-ray detector 18 detects the X-ray generated from the X-ray tube 16 which has transmitted through the subject P, and generates a current signal in accordance with the intensity of the detected X-ray. A data acquisition system (DAS) 26 is connected to the X-ray detector 18.

The DAS 26 acquires the current signal from the X-ray detector 18 under the control of the scanning controller 44. The DAS 26 amplifies the acquired current signal, performs digital conversion on the amplified current signal, and generates projection data. The projection data is transmitted to the computer 30 via a non-contact data transmission unit 28 each time it is generated. The scan unit 10 repeats the CT scan to generate the projection data in chronological order and transmits it to the computer 30.

The computer 30 comprises a preprocessor 32, a reconstruction unit 34, a real-time image generating unit 36, a monitoring image generating unit 38, a weight calculation part 40, a ROI SETTING UNIT 42, a scanning controller 44, a display 46, a console 48, a memory 50, and a system controller 52.

The preprocessor 32 applies preprocessing on the projection data (referred to as pure raw data) supplied from the DAS 26 on a real-time basis. The preprocessing includes logarithm conversion processing and sensitivity correction, etc. The preprocessing generates projection data to be used for image reconstruction. The pure raw data is preprocessed to create raw data.

In the embodiment, a calculation is performed using both the raw data and the pure raw data. The pure raw data is, in essence, data of an X-ray count value detected by the X-ray detector 18. The raw data is data obtained by performing logarithm conversion on the pure raw data. The raw data indicates a transmission length of the X-ray inside the subject.

The reconstruction unit 34 reconstructs the CT image based on the scan data (projection data or raw data) acquired by the scan unit 10 scanning the subject P. In other words, the reconstruction unit 34 reconstructs the CT image of the subject P based on the projection data (raw data) acquired by the X-ray irradiation at a first radiation dose when performing pre-scanning. In the following explanation, the CT image obtained by scanning the subject at the first radiation dose when performing pre-scanning is referred to as a reference image.

The reconstruction unit 34 reconstructs the CT image of the subject P on a real-time basis based on the projection data (raw data) acquired by the X-ray irradiation at a second radiation dose when performing monitoring scanning. In other words, the reconstruction unit 34 reconstructs the CT image in chronological order based on the projection data generated by the monitoring scanning in chronological order. In the following explanation, the CT image reconstructed on a real-time basis by scanning the subject at the second radiation dose when performing monitoring scanning is referred to as a real-time image.

In the embodiment, the second radiation dose for the monitoring scanning is set lower than the first radiation dose for pre-scanning.

The monitoring image generating unit 38 creates a monitoring image by superimposing (synthesizing) the reference image on the real-time image. In the existing techniques, a real-time image is displayed by the real-time image alone. However, in the embodiment, the monitoring image generating unit 38 creates a new image (monitoring image) by superimposing the reference image on the real-time image.

Preferably, the monitoring image generating unit 38 makes the color of the reference image and the color of the real-time image different. For example, a reference image in yellow can be superimposed on a real-time image in normal colors. In this manner, an operator (a user) would be able to distinguish the reference image from the real-time image.

The weight calculation part 40 calculates a weight for when the monitoring image generating unit 38 superimposes the reference image on the real-time image, for example, for each pixel of the reference image. In other words, the weight calculation part 40 calculates the distribution of the weight for when superimposing the reference image on the real-time image. That is, the weight calculation part 40 does not simply superimpose the reference image on the real-time image by the ratio of 1:1; the blend ratio is changed based on the state of the CT image.

When calculating the weight, the projection data which is not preprocessed, i.e. the pure raw data, is used. The calculated weight is sent to the monitoring image generating unit 38. The monitoring image generating unit 38 superimposes the reference image on the real-time image based on the weight distribution calculated by the weight calculation part 40. In this manner, the monitoring image is created.

The ROI SETTING UNIT 42 sets the ROI for the reconstructed CT image data. The ROI is set to a blood vessel region etc. where the radiocontrast agent flows. The ROI may be set automatically by the image processing, or may be set manually by an operator using the console 48. The ROI is set in chronological order at the same position on the CT image.

Specifically, the monitoring image generating unit 38 may have the real-time image displayed on the ROI. In other words, only in the case of the ROI, the real-time image as taken may be displayed without superimposing the reference image on the real-time image.

The scanning controller 44 controls the scan unit 10 in order to perform the X-ray CT scan on the subject P. The scanning controller 44 controls the scan unit 10 and switches the X-ray radiation dose between the first radiation dose and the second radiation dose. For example, switching between the pre-scan, monitoring scan, and main scan is an example of a control carried out by the scanning controller 44.

During the monitoring scan, the scanning controller 44 controls the scan unit 10 (specifically, the rotary driver 20, the high-voltage generator 22, the X-ray collimator 24, and the DAS 26) to continue with the monitoring scan. When a scan shift instruction is given, the scanning controller 44 controls the scan unit 10 (specifically, the rotary driver 20, the high-voltage generator 22, the X-ray collimator 24, and the DAS 26) to shift the scan mode from the monitoring scan to the main scan.

The display 46 displays the created reference image and the monitoring image, or a time density curve line of the radiocontrast agent on a display device. As the display device, it is possible to use, for example, a CRT display, a liquid crystal display, an organic EL display, or a plasma display.

The console 48 receives various commands or information input by the operator. For example, the console 48 acquires position information of the ROI set by the operator using an input device. As the input device, a keyboard, a mouse or a switch etc. may be used.

The memory 50 is a memory such as a RAM (Random Access Memory) or a ROM (Read Only Memory), and a storage device or a storage means such as a Hard Disk Drive (HDD). Other than a magnetic disc such as the HDD, a magnetic optical disc or an optical disc such as a CD (Compact Disc) and a DVD (Digital Versatile Disc) may be used.

The memory 50 stores the projection data, the CT image data, and the time density curve line data of the radiocontrast agent. The memory 50 stores a control program of the X-ray CT apparatus 1. The control program includes commands for realizing a new processing function related to the embodiment (the reconstruction unit 34, the real-time image generating unit 36, the monitoring image generating unit 38, and the weight calculation part 40 etc.).

The system controller 52 serves as the nerve center of the X-ray CT apparatus 1. Specifically, the system controller 52 reads out the control program stored in the memory 50, loads it in a memory, and controls each unit in accordance with a loaded machine language instruction string.

Each function of the preprocessor 32, the reconstruction unit 34, the real-time image generating unit 36, the monitoring image generating unit 38, the weight calculation part 40, the ROI setting unit 42, the scanning controller 44, the display 46 and the console 48 in the above configuration may, for example, be stored in the memory 50 in a form of program that is executable by the system controller 52.

By reading out the program from a memory circuitry (memory 50) and executing it, the system controller 52 comprises a processor which realizes a function corresponding to each program. In other words, a processing circuitry in a state where each program has been read out will comprise each function shown in the computer 30 of FIG. 1.

Instead of storing the program in the memory circuitry, it is also possible to integrate the program directly into the processing circuitry. In this type of form, the processor realizes the functions by reading out and executing the programs integrated in the circuitry.

FIG. 1 exemplifies the matter of the single computer 30 realizing the functions of the preprocessor 32, the reconstruction unit 34, the real-time image generating unit 36, the monitoring image generating unit 38, the weight calculation part 40, the ROI setting unit 42, the scanning controller 44, the display 46, and the console 48 by a single processor (system controller 52). Instead, it is also fine to configure a processing circuitry by combining a plurality of independent processors, and realize each function by having each processor execute the program.

The term "processor" used in the above explanation indicates, for example, a circuit of a CPU (central processing unit), a GPU (Graphics Processing Unit), or an Application Specific Integrated Circuit (ASIC), Programmable Logic Devices (for example, a Simple Programmable Logic Device (SPLD), a Complex Programmable Logic Device (CPLD), and a Field Programmable Gate Array (FPGA)).

The preprocessor 32, the reconstruction unit 34, the real-time image generating unit 36, and the monitoring image generating unit 38 are examples of a plurality of functions of the circuitry in the claims. The weight calculation part 40 is an example of a calculation function of the circuitry in the claims. The ROI setting unit 42 is an example of a setting unit in the claims. The scanning controller 44 is an example of a controller in the claims. The display 46 is an example of a displaying function of the circuitry in the claims. The memory 50 is an example of a memory in the claims.

Figure 2:
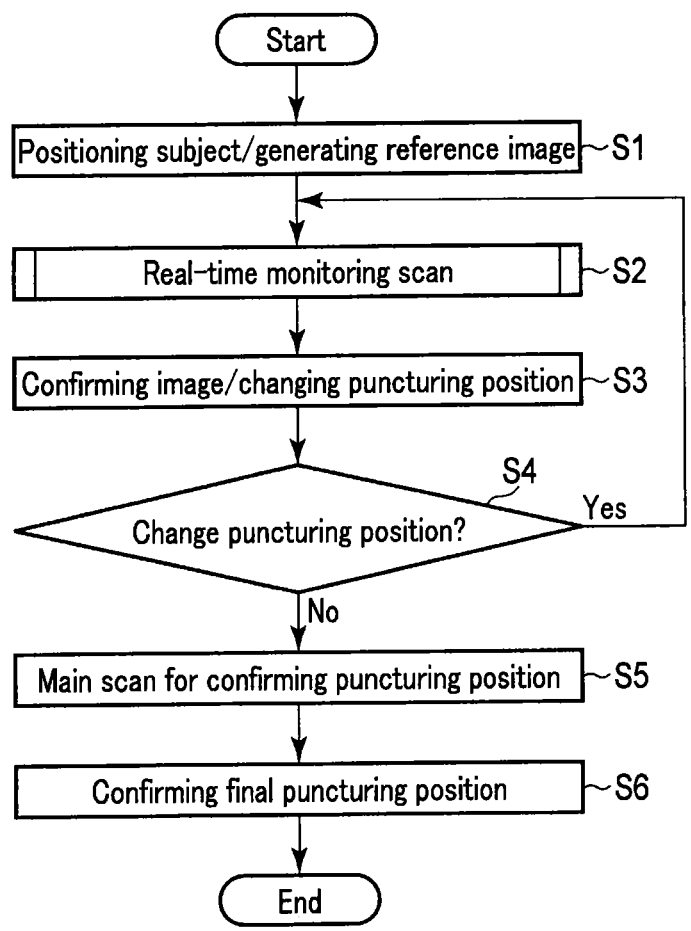
FIG. 2 is a flowchart showing an example of a scan sequence carried out by the X-ray CT apparatus 1 according to the embodiment.

FIG. 2 is a flowchart showing an example of a scan sequence carried out by the X-ray CT apparatus 1 according to the embodiment. The flowchart shown in FIG. 2 is an example of a work flow in the real-time monitoring scan for CT fluoroscopy. In FIG. 2, first of all, a pre-scan is executed to determine the position of a subject (a patient etc.) to create a reference image (step S1).

Subsequently, an operator operates the X-ray CT apparatus 1 to execute real-time monitoring scan (step S2). An operator performing surgery changes the puncturing position if necessary while confirming the real-time image (step S3). If the puncturing position is changed (Yes, in step S4), the processing procedure returns to step S2, and the real-time monitoring scan is executed again.

Subsequently, a main scan for confirming the puncturing position is executed by increasing the tube voltage (step S5). Based on the main scan image acquired here, the operator conclusively confirms the puncturing position (step S6).

Figure 3:
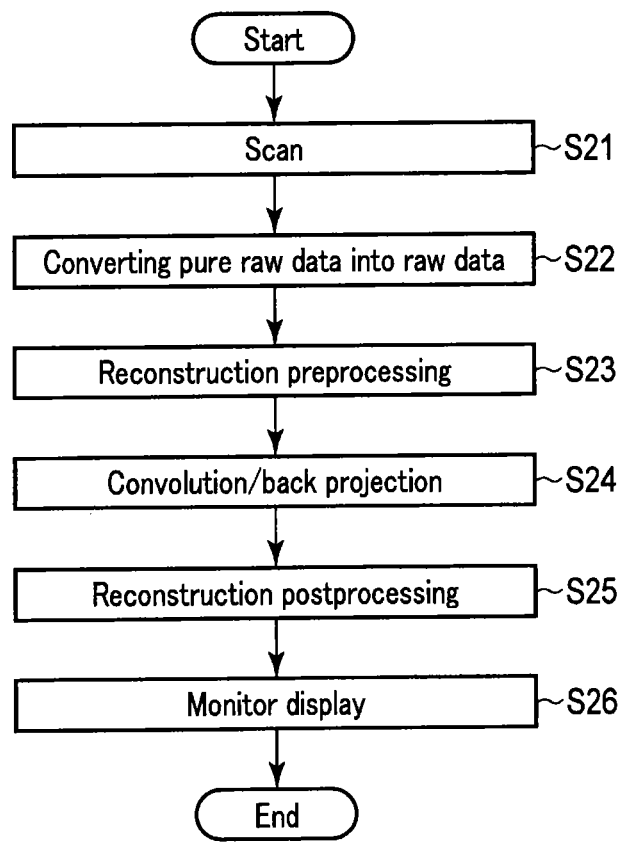
FIG. 3 is a flowchart showing an example of a processing procedure in step S2 of FIG. 2.

FIG. 3 is a flowchart showing an example of a processing procedure in step S2 (real-time monitoring scan) of FIG. 2. In the real-time monitoring scan, the pure raw data acquired by a scan (step S21) is Logarithm converted, thereby creating raw data (step S22). Reconstruction preprocessing is performed to create the CT image (step S23).

Subsequently, the CT image is created via a convolution operation (convolution), back projection (step S24), and reconstruction post-processing (step S25). The CT image is displayed on the display 46 (step S26). In the real-time monitoring scan, the above procedures are performed on a real-time basis.

Figure 4:
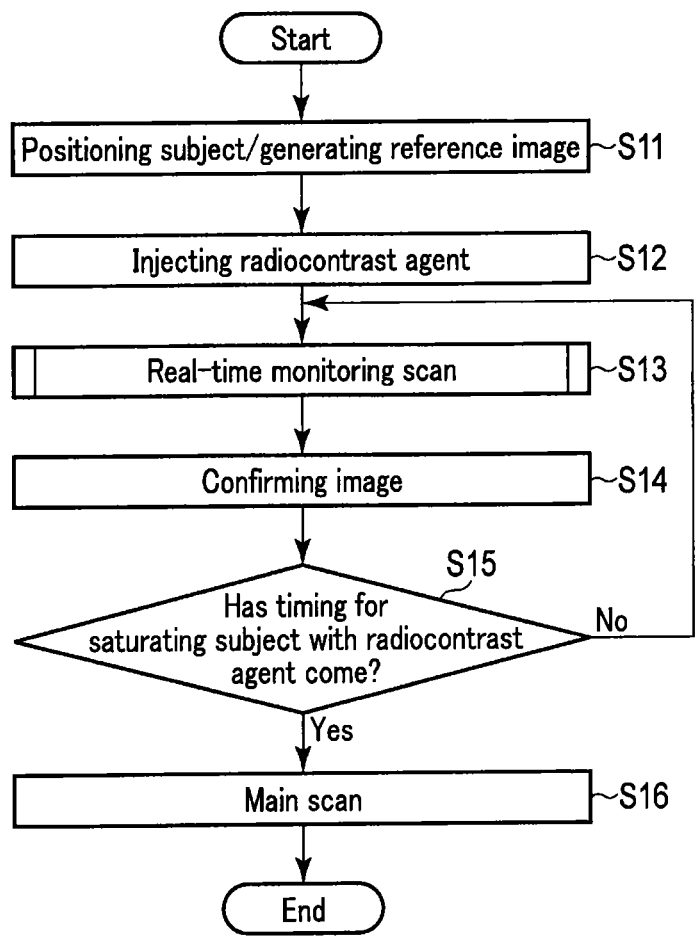
FIG. 4 is a flowchart showing another example of a scan sequence carried out by the X-ray CT apparatus 1 according to the embodiment.

FIG. 4 is a flowchart showing another example of a scan sequence carried out by the X-ray CT apparatus 1 according to the embodiment. The flowchart shown in FIG. 4 is an example of a work flow in the monitoring scan. In FIG. 4, first of all, a pre-scan is executed to determine the position of a subject, thereby creating a reference image (step S11). When the positioning is completed, a radiocontrast agent starts to be injected into the subject (step S12).

Subsequently, the operator operates the X-ray CT apparatus 1 to execute the real-time monitoring scan in the same procedures as in FIG. 3 (step S13). While confirming the real-time image acquired in this manner (step S14), the operator determines the timing at which the subject becomes saturated with the radiocontrast agent (step S15). If the image processing performance of the computer 30 is sufficient, the operator may entrust the computer 30 to determine this timing.

When the timing of the radiocontrast agent saturation is determined to have arrived (Yes, in step S15), the operator operates the X-ray CT apparatus 1 and switches the tube voltage to start the main scan (step S16).

Figure 5:
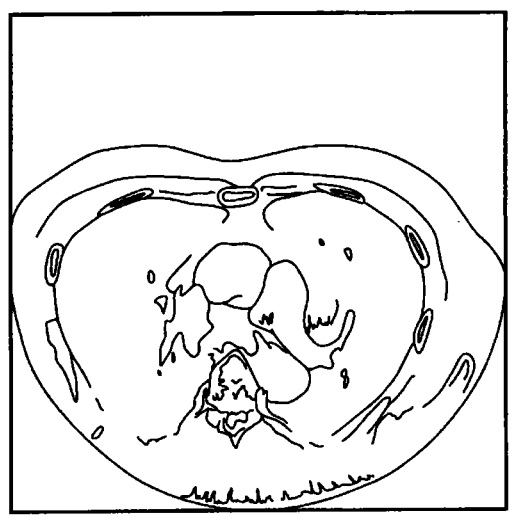
FIG. 5 is a diagram showing an example of a low radiation dose image.

In the real-time monitoring scan, the X-ray radiation dose is lowered as much as possible. Therefore, as shown in FIG. 5, the image may be degraded by a mixed noise, including structural deformation etc., thereby creating an image (low radiation dose image) that is difficult to use for diagnostic reading. In the embodiment, a technique that is capable of overcoming such negative effects will be explained.

Figure 6:
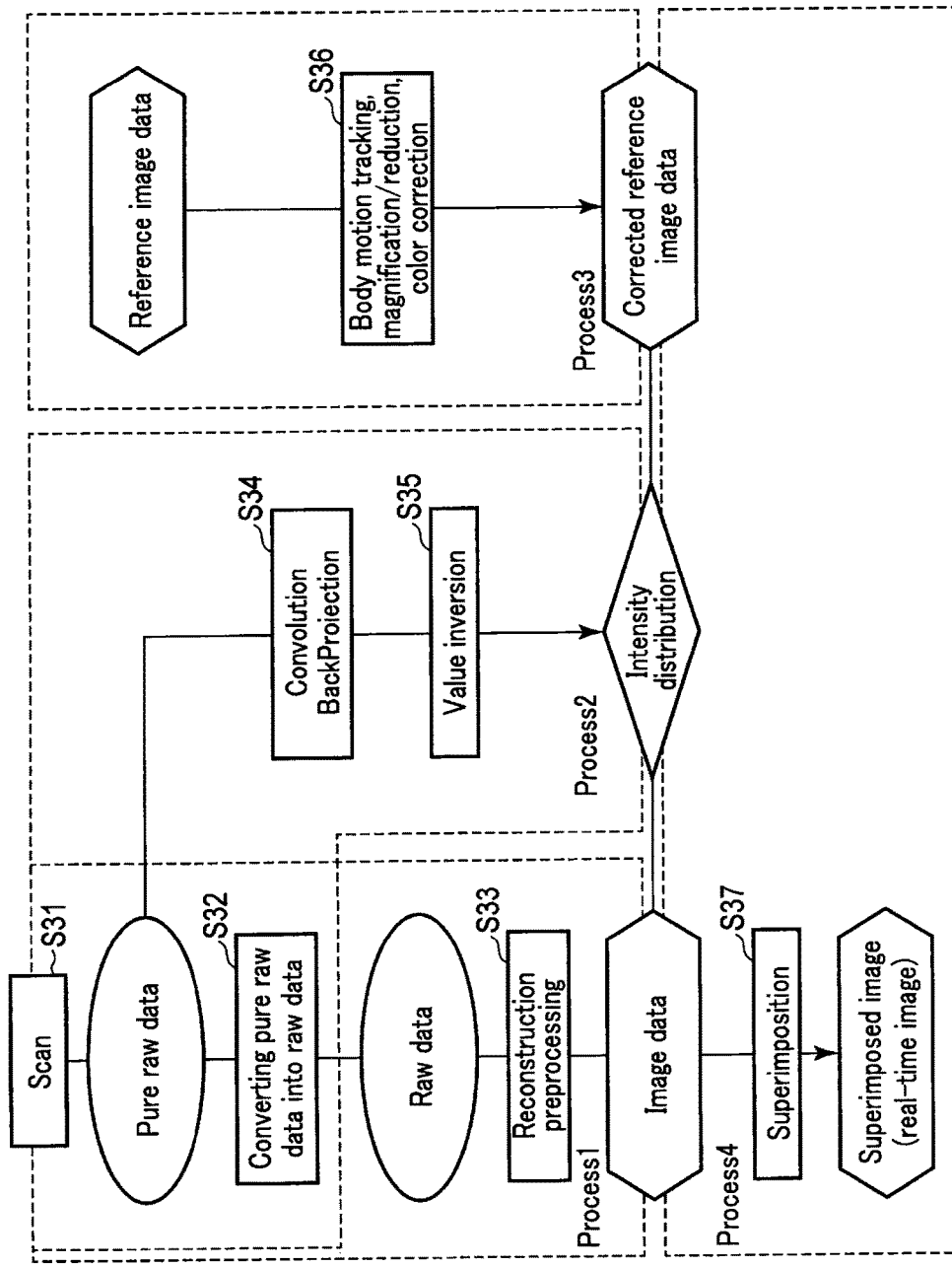
FIG. 6 is a flowchart showing an example of a processing procedure related to creating a real-time image.

FIG. 6 is a flowchart showing an example of a processing procedure related to creating a real-time image. The flowchart shown in FIG. 6 includes Processes 1 to 4.

In FIG. 6, Process 1 relates to the creation of the CT image data, which includes the procedures of steps S31, S32, and S33. In other words, after the pure raw data is acquired by the scan (step S31), the pure raw data is converted into raw data by the logarithm conversion processing (step S32).

Subsequently, the X-ray CT apparatus 1 performs reconstruction processing (step S33) to reconstruct the CT image from the raw data. The reconstruction processing includes the reconstruction preprocessing, the convolution/back projection, and the reconstruction post-processing for the raw data.

Process 2 is for obtaining a weight for superimposing the reference image on the real-time image, which includes the procedures of steps S34 and S35. In other words, the X-ray CT apparatus 1 applies convolution/back projection directly to the pure raw data acquired by the scan of step S31 (step S34).

The processing of step S34 acquires the intensity distribution which directly reflects the count value of the X-ray (pure raw data). This distribution indicates the degree of image quality deterioration in the CT image. That is, for portions where the degree of deterioration is large, a lower value is distributed, and for portions of clear vision, a higher value is distributed. This value can be defined, for example, in units of pixels. For portions indicating a lower value, for example, an X-ray high-absorbent body is considered to be distributed.

Subsequently, the X-ray CT apparatus 1 standardizes the intensity distribution acquired in step S34, and also inverts the standardized value (step S35). An inversion processes value 1 into 0, and value 0 into 1. By this processing, a higher value will be distributed for portions with a higher degree of image quality deterioration, and a lower value will be distributed for portions that can be clearly seen. This distribution, in other words, is the weight distribution for when superimposing the reference image on the real-time image.

Process 3 is the preprocessing for superimposing the reference image on the real-time image. Process 3 includes a well-known processing such as body motion tracking, magnification/reduction, and color correction (step S36).

Figure 7:
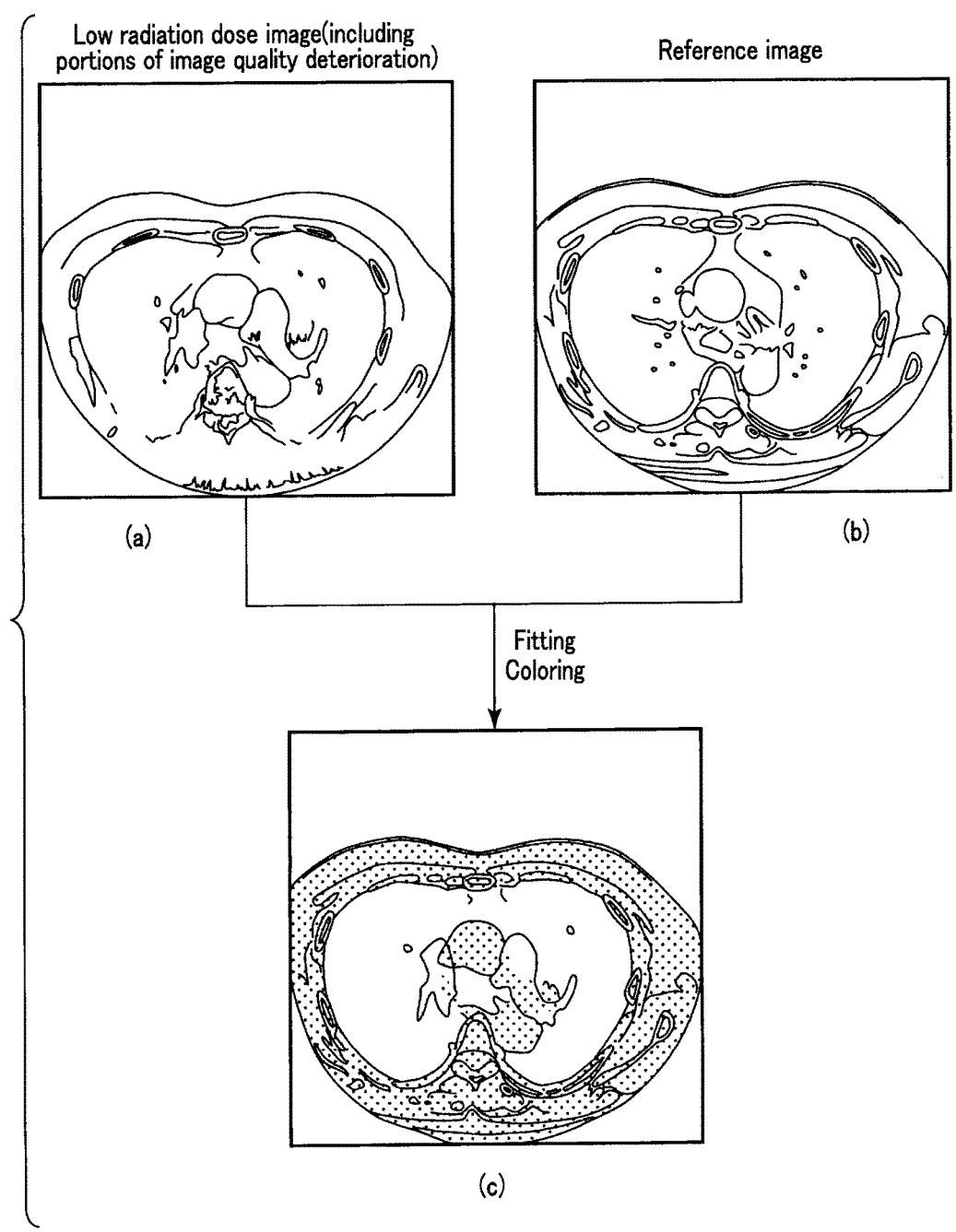
FIG. 7 shows diagrams showing an example of a low radiation dose image, an example of a reference image and a monitoring image created on the basis of the low radiation dose image and the reference image.

For example, in many cases, the body motion of the subject may cause inconsistency between the shape of the low radiation dose image (real-time image) shown in FIG. 7. Also, the shape of the reference image is shown in FIG. 7. Here, the shape includes an outline and a position of an organ etc. Therefore, in Process 3, the shape of the reference image is corrected (fitting) to create reference image data which is capable of being superimposed on the real-time image.

Process 4 is a process for superimposing the corrected reference image on the real-time image, and includes the processing of step S37. In other words, the X-ray CT apparatus 1 multiplies a pixel value of each pixel configuring the corrected reference image data by the intensity distribution obtained in Process 2, to form image data for superimposing. The X-ray CT apparatus 1 colors the image data for superimposing and superimposes it on the real-time image (step S37).

The superimposed image created in this manner is, in other words, the real-time image. FIG. 7 shows a diagram showing an example of the real-time image(c). This real-time image is displayed on the display 46 (FIG. 1). By repeating Processes 1 to 4 on a real-time basis, the real-time image can be created in real-time as shown in FIG. 7.

FIG. 8A and FIG. 8B are schematic diagrams for supplemental explanation on the intensity distribution. As shown in FIG. 8A, many subjects include a region (for example, high-absorbent body) in which the image quality deteriorates at a low radiation dose. The count value of the pure raw data of a path transmitting through this region becomes significantly lower than the count value of a path transmitting through air or a substance of low density. This is caused in part by the X-ray being attenuated in an exponential manner.

In the existing CT image reconstruction technique, the count value of each path (pure raw data) is logarithm converted to generate raw data which reflects an integration value of a transmission length of various substances in each path. This raw data is subject to convolution processing and back projection processing to reconstruct the CT image.

In contrast, in the present embodiment, the convolution processing and the back projection processing are not performed on the raw data, but on the pure raw data which is obtained in the previous stage. In this manner, so to say, the intensity distribution of the X-ray count value can be obtained. This intensity distribution indicates a lower value in a region where the count value of the pure raw data is low (low radiation dose portion), that is, in a region where the image quality deteriorates. By standardizing this intensity distribution, and also inverting the standardized value, a weight distribution in which the value becomes higher in the low image quality region can be created (FIG. 8B). By superimposing the reference image on the real-time image by the blend ratio based on this weight distribution, it is possible to generate a monitoring image in which the reference image appears stronger as the image quality of the region becomes lower.

Figure 9:
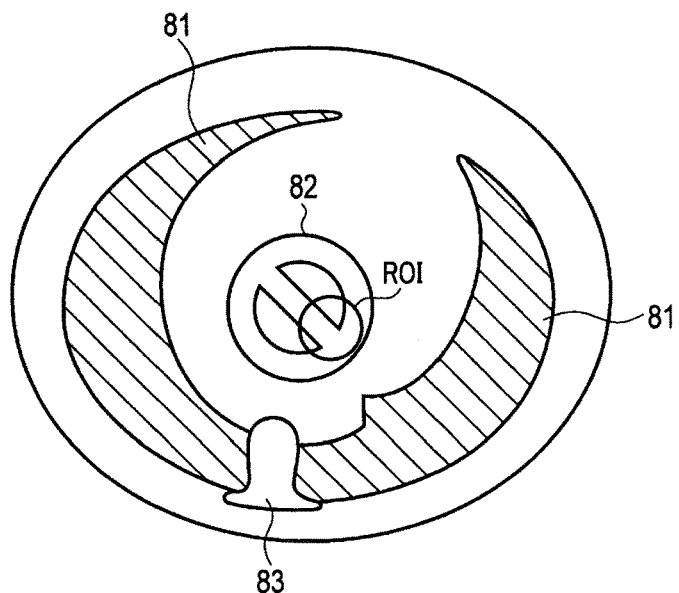
FIG. 9 is a schematic diagram showing an example of a reference image.

FIG. 9 to FIG. 12 are schematic diagrams showing an example of the image created in the embodiment. FIG. 9 shows an example of a reference image displayed on the display 46, which includes a lung region 81 and a spine region 83. This reference image is assumed to be photographed under a condition of a comparatively high radiation dose that is enough for the organ 82 which is an anatomical segment inside the subject P to be clearly shown. The operator sets the ROI to, for example, a part of the organ while observing the reference image.

Figure 10:
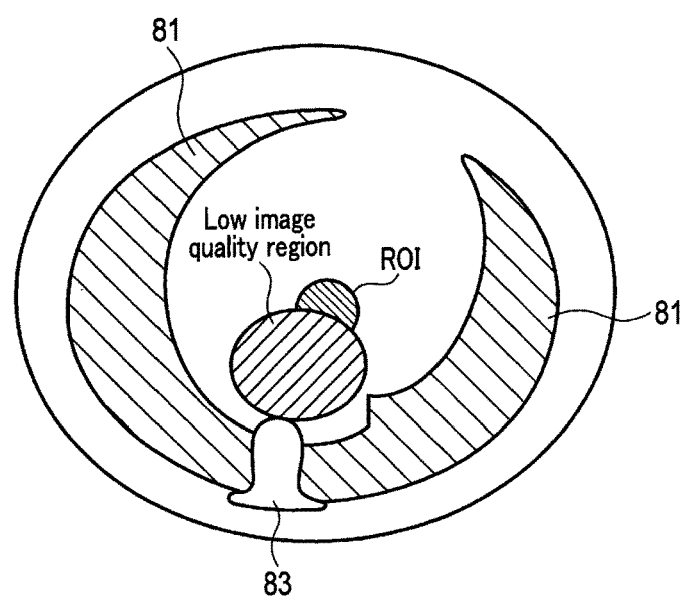
FIG. 10 is a schematic diagram showing an example of a real-time image.
Figure 11:
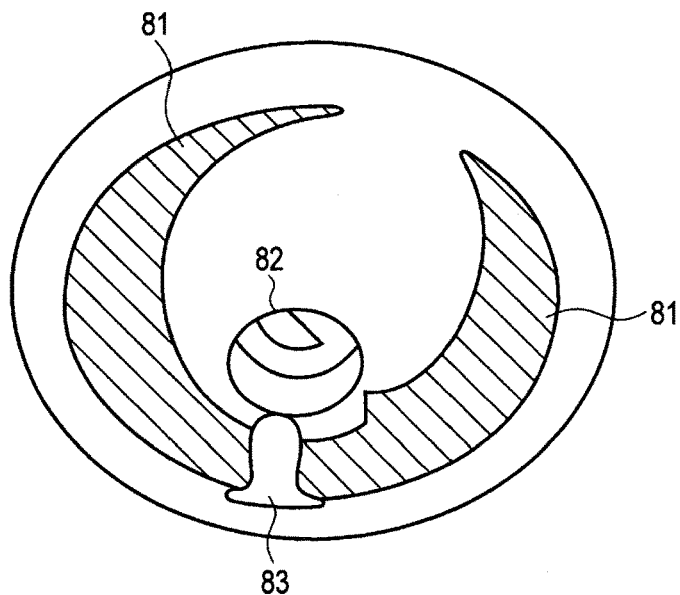
FIG. 11 is a schematic diagram showing an example of a real-time image.

FIG. 10 is a diagram showing an example of the real-time image generated in the monitoring scan after the pre-scan. Since this scan is performed by a low radiation dose, most of the real-time images include a low image quality region. Since the weight of the reference image in the low image quality region becomes higher, for example, as shown in the monitoring image of FIG. 11, the organ 82 becomes clearly projected.

Figure 12:
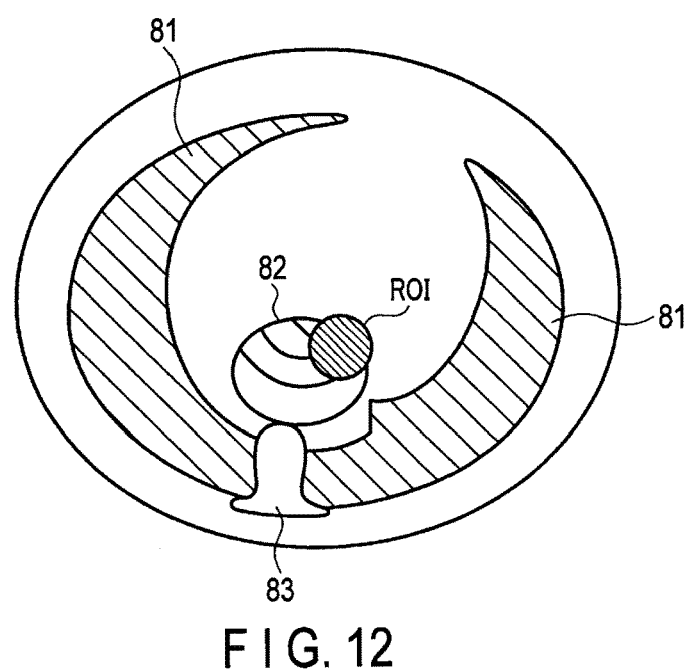
FIG. 12 is a schematic diagram showing an example of a real-time image.

However, under the condition in which the ROI overlaps the low image quality region, the real-time image may be displayed on the ROI in the manner shown in FIG. 12. In other words, it is fine to increase the priority of the real-time image in the ROI to display the real-time image instead of the reference image. At a clinical site, there is a need to observe a real-time image on a priority basis. This aspect of the display is capable of responding to such need.

As explained above, in the present embodiment, the reference image acquired by the pre-scan is superimposed in a different color on the low radiation dose image (real-time image) acquired by real-time monitoring scan. When doing so, the color intensity (weight of superimposing) is changed in accordance with an X-ray count amount acquired at the X-ray detector 18. This weight distribution is reflected in, for example, the color shading. The weight distribution is calculated without performing logarithm conversion on the count amount, that is, by inverting the value obtained by performing back projection directly on the count value of the pure raw data. Furthermore, when superimposing the reference image on the real-time image, a correction in line with the body motion tracking and the size of the body is added.

As mentioned above, according to the present embodiment, an X-ray CT apparatus and a medical image display apparatus which can improve visibility of the image created by a low radiation dose scan can be provided. In this manner, diagnostic reading can be realized with high reproducibility, without depending on the technique of a user, an operator, or a diagnostic reading doctor, thereby reducing human errors and encouraging improvement in safety issues, etc. Furthermore, it will be possible to improve the reconstruction work flow and ascertain information on the deteriorated low radiation dose image.

First Modified Example

Figure 13:
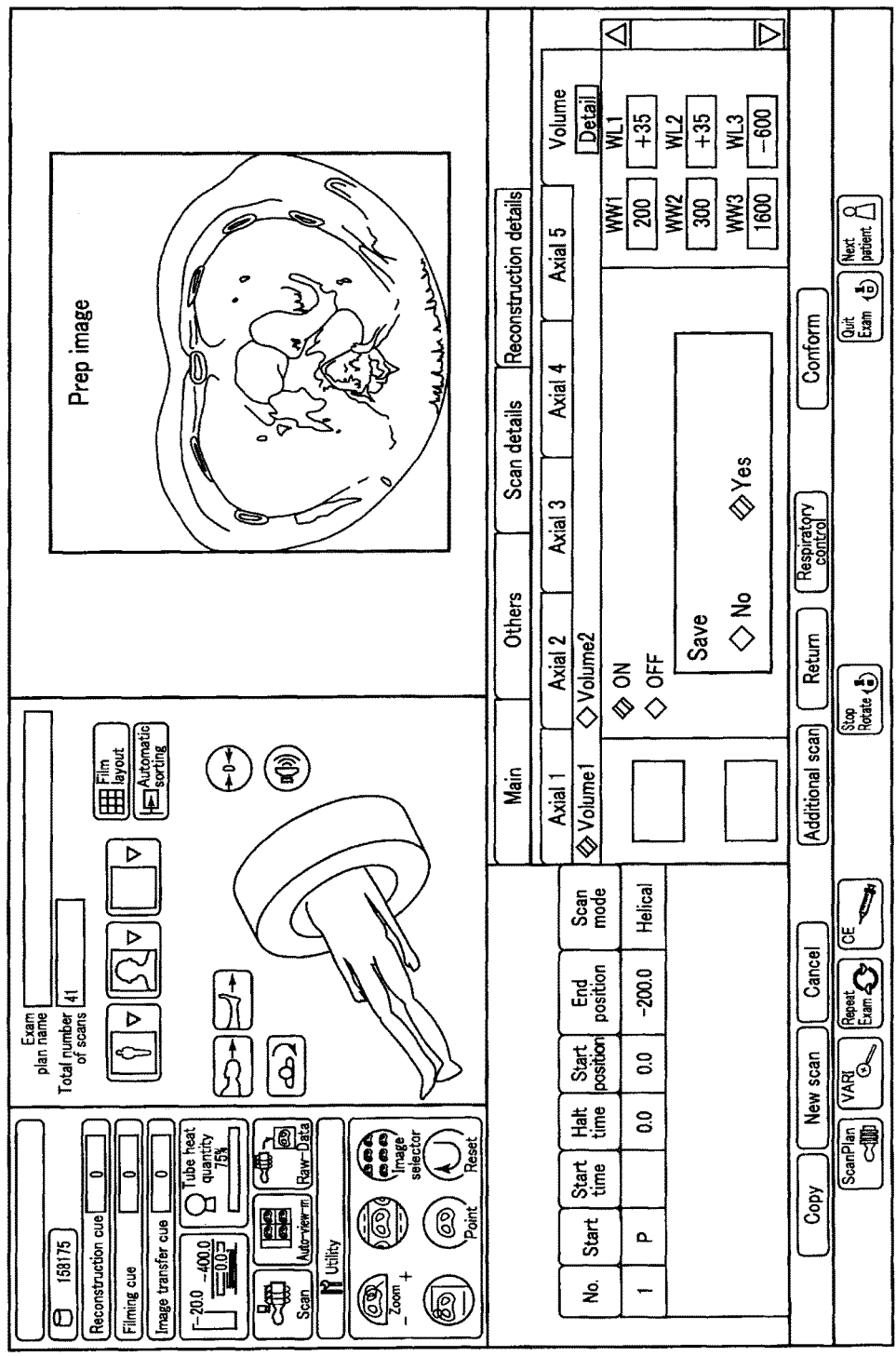
FIG. 13 shows a first example of a console window displayed on a display 46.

FIG. 13 shows a first example of a console window displayed on a display 46. This window shows an example of a so-called prep window. The prep window shows a prep cross-section surface obtained by pre-scanning. When a monitoring scan is started, the monitoring of a CT value at a ROI set in the prep cross-section surface is started with the injection of a radiocontrast agent. As soon as the CT value exceeds a defined value, a main scan is started. This enables a user to obtain an image dyed with the radiocontrast agent to the intended extent.

Figure 14:
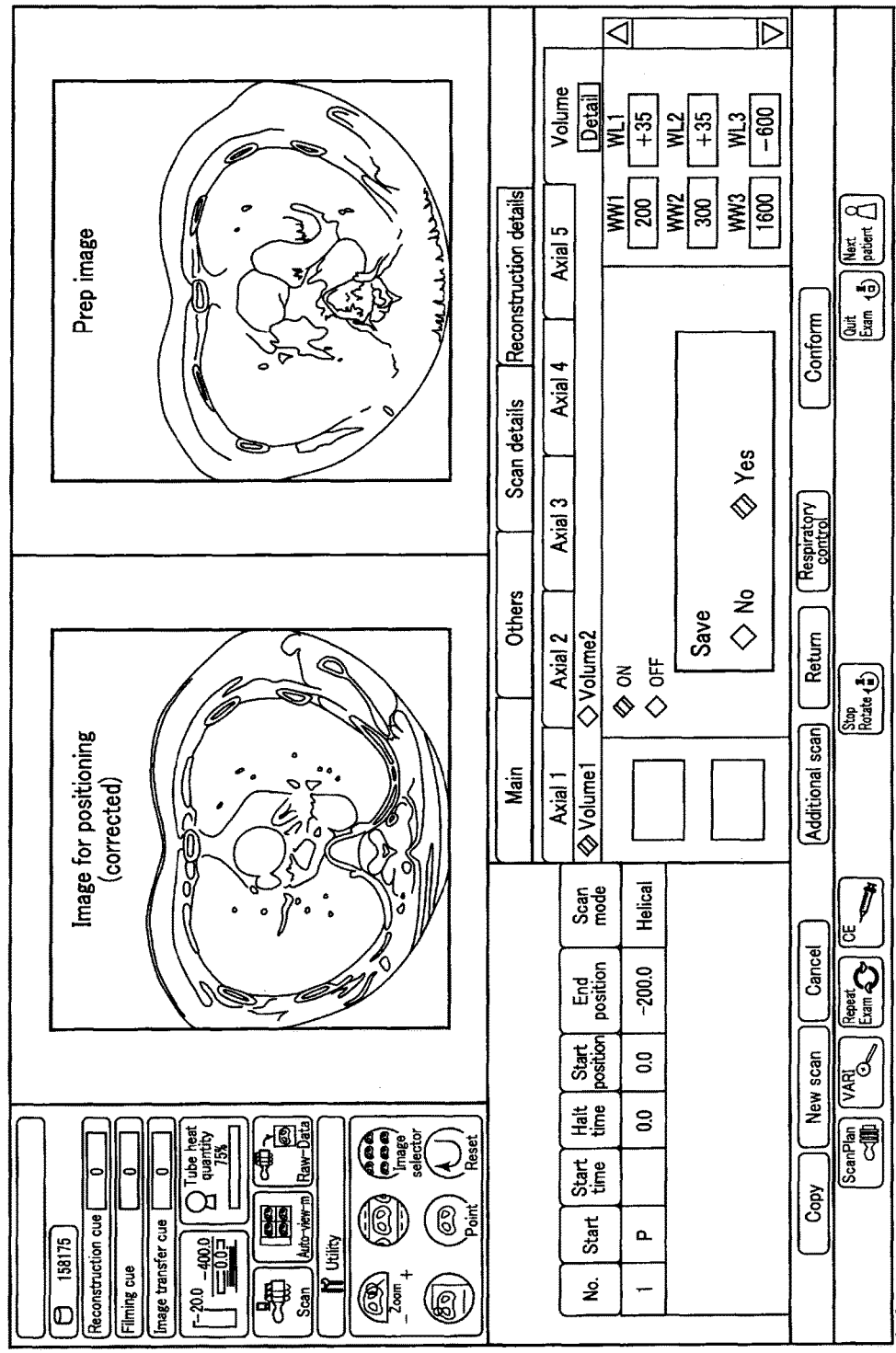
FIG. 14 shows a second example of a console window displayed on the display 46.

FIG. 14 shows a second example of a console window displayed on the display 46. As shown in FIG. 14, an image corrected to match the position of a prep image may be displayed in a common console window. In order to realize this, a real-time image generating unit 36 corrects (position adjustment etc.) a reference image (an image for positioning) obtained by pre-scanning a subject with a first radiation dose in accordance with the prep image. In this manner, a corrected image for positioning is created on a real-time basis. By displaying the prep image and the corrected image for positioning in a common console window in this manner, a user (a doctor etc.) would be able to determine the state of the subject with greater accuracy.

Second Modified Example

Figure 15:
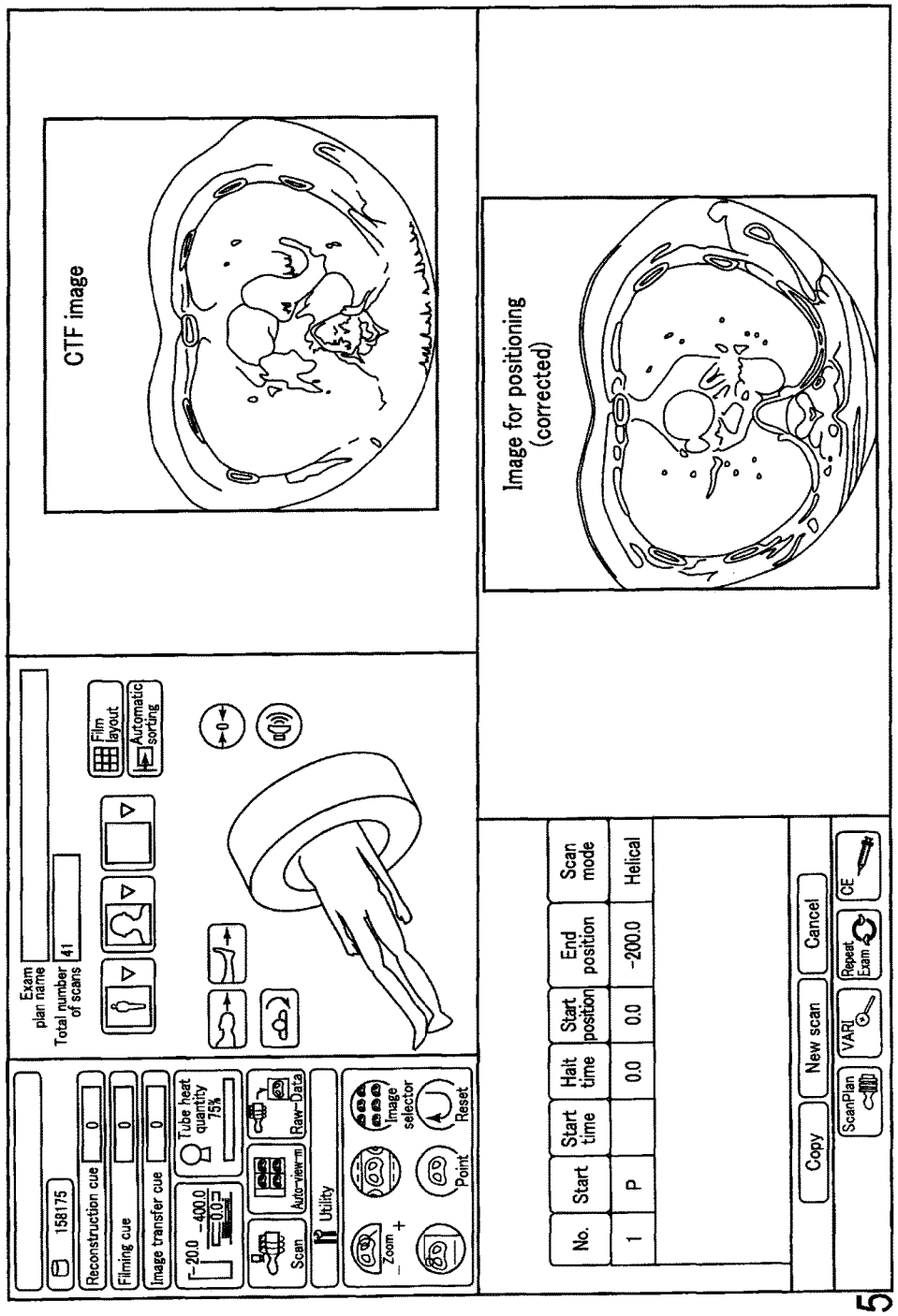
FIG. 15 shows a third example of a console window displayed on the display 46.

FIG. 15 shows a third example of a console window displayed on the display 46. As shown in FIG. 15, a real-time image acquired by CT fluoroscopy (CTF) and the corrected image for positioning may be displayed on a common console image. In this manner, a user (a doctor etc.) would be able to determine the state of the subject with greater accuracy.

Figure 16:
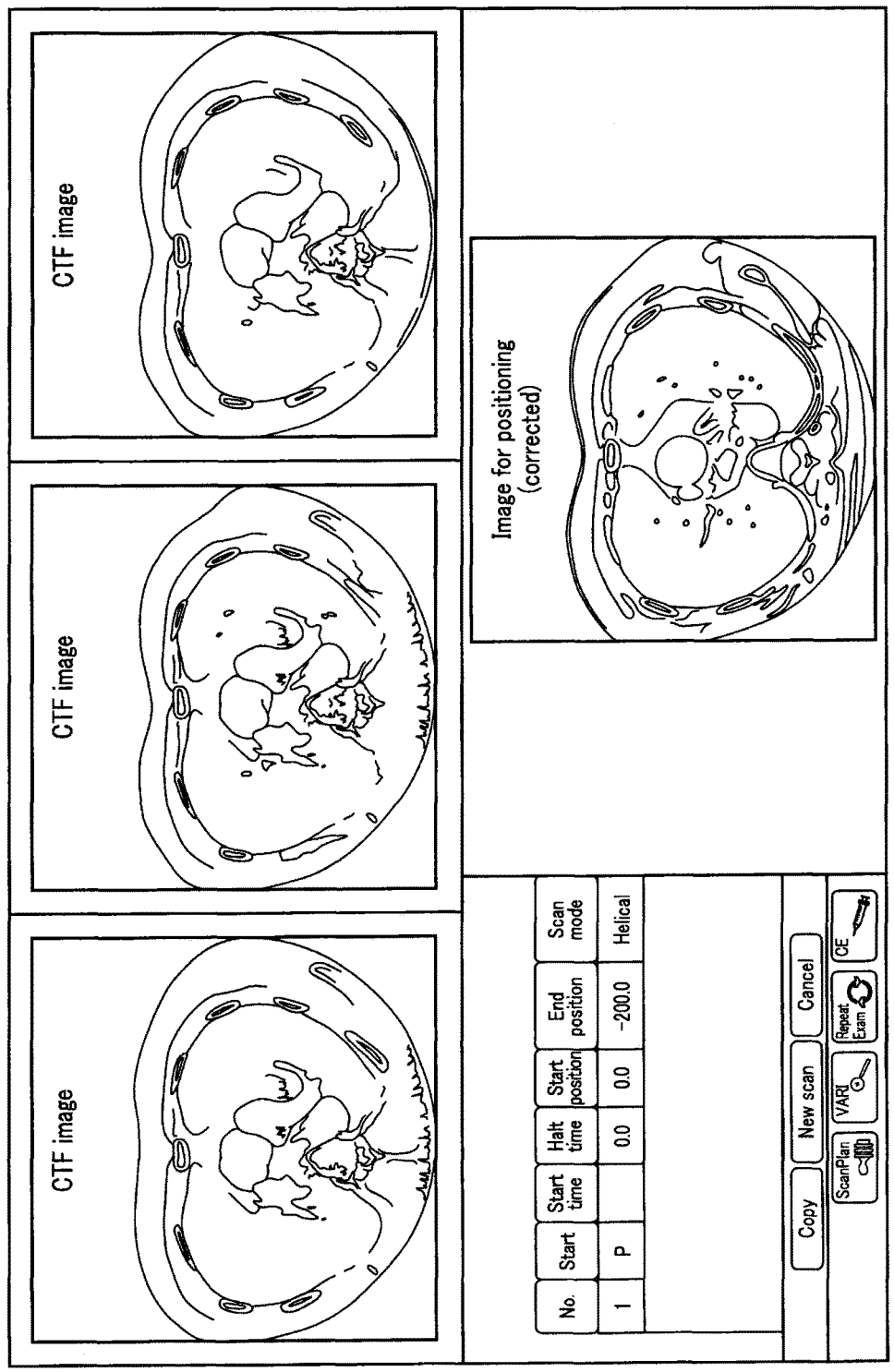
FIG. 16 shows a fourth example of a console window displayed on the display 46.

FIG. 16 shows a fourth example of a console window displayed on the display 46. As shown in FIG. 16, for example, three CT fluoroscopy images corresponding to three different cross-section surfaces of an axial image may be displayed with the corrected image for positioning in a common console window.

Figure 17:
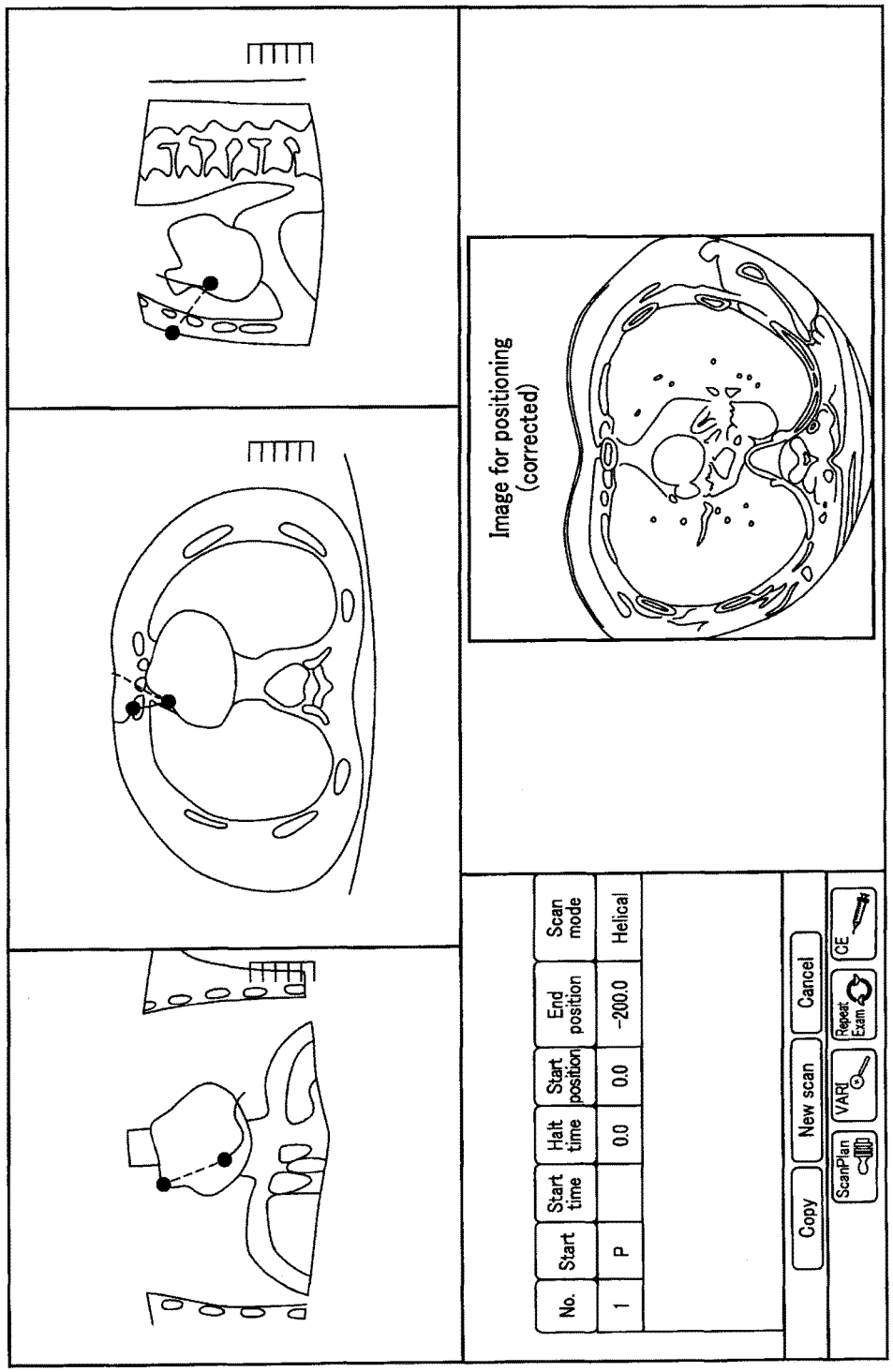
FIG. 17 shows a fifth example of a console window displayed on the display 46.

Alternatively, as shown in the fifth example of FIG. 17, in addition to the axial image, a coronal cross-section surface image and a sagittal cross-section surface image may be displayed with the corrected image for positioning in a common console window.

For example, the CT fluoroscopy is used in the case of confirming the positional relation between the distal end portion of a puncture needle and a portion of a sample to be collected during biopsy. When performing CT fluoroscopy, during the same study, a scan for determining the puncturing position and a monitoring scan for confirming the state of the puncture are executed. Also in the CT fluoroscopy, the monitoring scan is executed with a radiation dose that is lower than a radiation dose for a scan for positioning.

By referring to the windows of FIG. 16 and FIG. 17, the user is able to clearly grasp the position of the distal end of the puncture needle and the positional relation between the distal end and the target. In other words, the user will be able to determine the condition of the puncture with greater accuracy.

Third Modified Example

Figure 18:
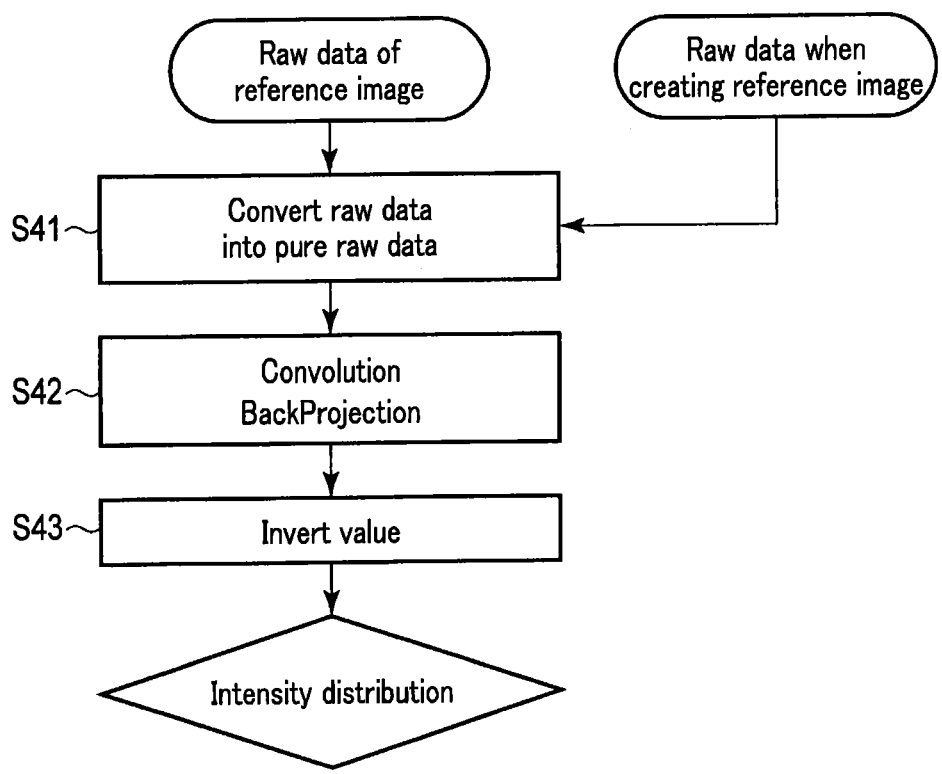
FIG. 18 is a flowchart showing another example of a processing procedure related to creating a real-time image.

FIG. 18 is a flowchart showing another example of a processing procedure related to creating a real-time image. Based on the flowchart shown in FIG. 18, a procedure of acquiring intensity distribution data based on a scan result of the reference image, that is, the scan result of the scan for positioning, will be explained.

Raw data of the reference image and raw data obtained when creating the reference image are converted respectively into pure raw data (step S41). Subsequently, an X-ray CT apparatus 1 applies convolution/back projection directly to the pure raw data obtained by a calculation performed in step S41 (step S42).

By the processing of step S42, the intensity distribution which directly reflects a count value (pure raw data) of an X-ray in the scan for positioning is acquired. Subsequently, the X-ray CT apparatus 1 standardizes the intensity distribution acquired in step S42, and, further, inverts the standardized value (step S43). In this manner, a weight distribution (intensity distribution) for when superimposing the reference image on the real-time image is obtained.

Figure 19:
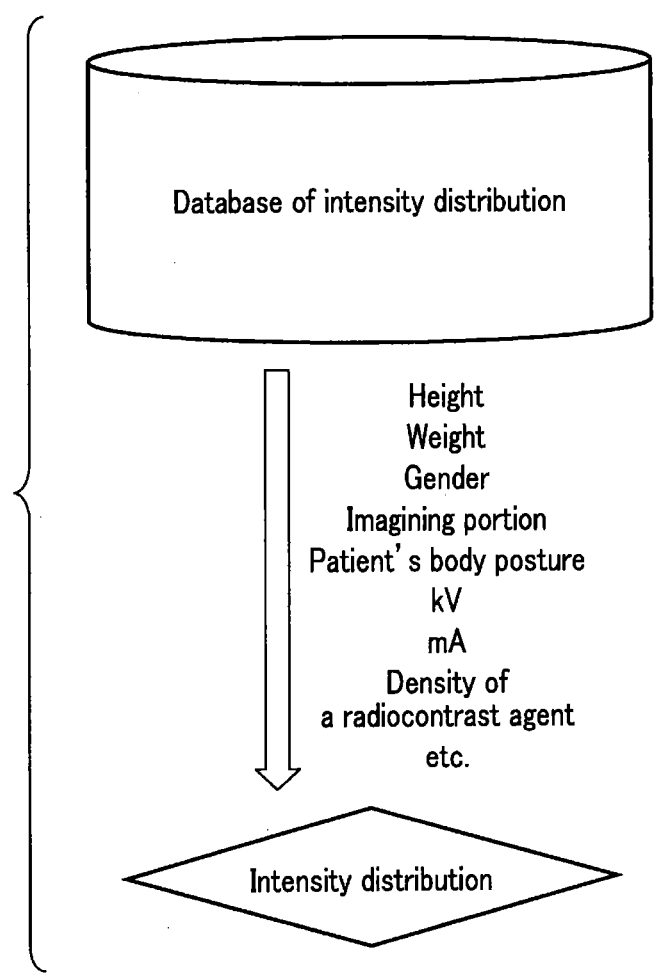
FIG. 19 is a schematic diagram showing another example of a method of obtaining an X-ray intensity distribution in a subject.

The intensity distribution may also be obtained without using projected data acquired by the scan. For example, as shown schematically in FIG. 19, a databased of the intensity distribution may be provided in a hospital network, inside the X-ray CT apparatus 1, or in an external network (a so-called cloud computing system), in a state where the intensity distribution data is, for example, associated with a scan condition, and stored in advance in this database. The scan condition includes, for example, height, weight, gender, imaging portion, patient's body posture, tube voltage (kV), tube current (mA), and density of a radiocontrast agent. When conducting a study, optimal intensity distribution data may be acquired from the list of intensity distribution data within the database with the scan condition as a key. This also makes it possible to acquire intensity distribution (weight distribution) data which can be used for shape correction (fitting) or superimposing a plurality of images.

The present invention is not limited to the above embodiments. For example, as shown in FIG. 12, in some cases the step at the boundary portion of the ROI is extremely large. This step indicates a discontinuity between the superimposed real-time image and the reference image. In such case, the discontinuity may be resolved (or interpolated) by an image processing based on an interpolation curve (sigmoid curve etc.). In this manner, a more natural CT image can be provided.

In the embodiments, examples of CT fluoroscopy and monitoring scan have been explained. The techniques of the embodiments are not restrictive and are applicable to the real-time monitoring image processing in any case. Furthermore, the techniques of the embodiments are applicable without being limited to the scan at low radiation doses.

While certain embodiments of the inventions have been described, these embodiments have been presented by way of examples only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The appended claims and their equivalents are intended to cover such forms or modifications as would fall within the scope and spirit of the inventions.

The invention claimed is:

1. An X-ray computed tomography apparatus, comprising:
an X-ray generator comprising an X-ray tube;
a high-voltage generator configured to generate a tube voltage to be applied to the X-ray tube;
an X-ray detector configured to detect X-rays irradiated from the X-ray tube and transmitted through a subject;
a controller configured to control the high-voltage generator to scan the subject; and
circuitry configured to:
generate a reference image based on projection data acquired by a pre-scan;
generate real-time monitor images based on projection data acquired by a monitor scan which is executed after the pre-scan at a same study as the pre-scan;
generate superimposed images which have higher visibility than the real-time monitor images by synthesizing at least a part of the reference image and each real-time monitor image based on a weighted distribution, the weighted distribution being obtained by standardizing and inverting intensity distribution data;

control a display to display the superimposed images in a window;

determine a timing of a main scan which is executed at the same study as the pre-scan and the monitor scan in accordance with the superimposed images; and generate a main scan image based on projection data acquired by the main scan.

2. The X-ray computed tomography apparatus of claim 1, wherein the circuitry is configured to:

generate the reference image based on the projection data acquired by the pre-scan at a first radiation dose; and generate the real-time monitor images based on the projection data acquired by the monitor scan at a second radiation dose which is lower than the first radiation dose.

3. The X-ray computed tomography apparatus of claim 1, wherein the circuitry is configured to correct the reference image in accordance with each real-time monitor image.

4. The X-ray computed tomography apparatus of claim 1, wherein the circuitry is configured to:

calculate the weight distribution for synthesizing the reference image and each real-time monitor image; and synthesize the reference image and each real-time monitor image based on the calculated weight distribution.

5. The X-ray computed tomography apparatus of claim 4, wherein the circuitry is configured to calculate the weight distribution based on the projection data acquired by the monitor scan.

6. The X-ray computed tomography apparatus of claim 5, wherein the circuitry is configured to:

create the intensity distribution data by applying convolution and back projection on a count value of the projection data acquired by the monitor scan; and calculate the weight distribution based on the created intensity distribution data.

7. The X-ray computed tomography apparatus of claim 4, wherein the circuitry is configured to calculate the weight distribution based on the projection data acquired by the pre-scan.

8. The X-ray computed tomography apparatus of claim 1, wherein the circuitry is configured to create the superimposed images by making the colors different between the reference image and each real-time monitor image.

9. The X-ray computed tomography apparatus of claim 1, further comprising:

a memory configured to store the weight distribution in correspondence with a scan condition, wherein the circuitry is configured to synthesize the reference image and each real-time monitor image based on the weight distribution corresponding to the scan condition.

10. The X-ray computed tomography apparatus of claim 1, further comprising:

a setting unit configured to set a region of interest, wherein the circuitry is configured to display each real-time monitor image on the region of interest set in the superimposed images.

11. The X-ray computed tomography apparatus of claim 10, wherein the circuitry is configured to create an image which resolves a discontinuity at a boarder portion of the region of interest.

12. A medical image display apparatus, comprising:

a controller configured to cause an X-ray computed tomography apparatus to scan a subject; and circuitry configured to:

generate a reference image based on projection data acquired by a pre-scan;

generate real-time monitor images based on projection data acquired by a monitor scan which is executed after the pre-scan at a same study as the pre-scan;

generate superimposed images which have higher visibility than the real-time monitor images by synthesizing at least a part of the reference image and each second real-time monitor image based on a weighted distribution, the weighted distribution being obtained by standardizing and inverting intensity distribution data;

control a display to display the superimposed images in a window;

determine a timing of a main scan which is executed at the same study as the pre-scan and the monitor scan in accordance with the superimposed images; and generate a main scan image based on projection data acquired by the main scan.

13. The medical image display apparatus of claim 12, wherein the circuitry is configured to correct the reference image in accordance with each real-time monitor image.

14. The medical image display apparatus of claim 12, wherein the circuitry is configured to:

calculate the weight distribution for synthesizing the reference image and the real-time monitor images; and synthesize the reference image and each real-time monitor image based on the calculated weight distribution.

15. The medical image display apparatus of claim 14, wherein the circuitry is configured to calculate the weight distribution based on the projection data acquired by the monitor scan.

16. The medical image display apparatus of claim 14, wherein the circuitry is configured to calculate the weight distribution based on the projection data acquired by the pre-scan.

17. The medical image display apparatus of claim 12, further comprising:

a memory configured to store the weight distribution in correspondence with a scan condition, wherein the circuitry is configured to synthesize the reference image and each real-time monitor image based on the weight distribution corresponding to the scan condition.

* * * * *